United States Patent [19]

Husslein et al.

[11] 4,348,534
[45] Sep. 7, 1982

[54] PREPARATION OF 2-ARYLOXY-2-HALOPROPTONIC ACID COMPOUNDS

[75] Inventors: Gerd Husslein, Bad Durkheim; Gerhard Hamprecht, Weinheim, both of Fed. Rep. of Germany

[73] Assignee: BASF Aktiengesellschaft, Ludwigshafen, Fed. Rep. of Germany

[21] Appl. No.: 274,493

[22] Filed: Jun. 17, 1981

[30] Foreign Application Priority Data

Jul. 29, 1980 [DE] Fed. Rep. of Germany ....... 3028625

[51] Int. Cl.$^3$ ............................................. C07C 69/76
[52] U.S. Cl. ........................................ 560/62; 560/21; 560/23; 562/434; 562/466; 562/472; 564/170; 564/171; 260/465 D
[58] Field of Search ................. 560/62; 562/434, 466, 562/472; 564/170, 171

[56] References Cited

U.S. PATENT DOCUMENTS 3,546,273 12/1970 Bolhofer .............................. 560/62
4,153,803 5/1979 Thiele et al. ......................... 560/62

FOREIGN PATENT DOCUMENTS 54-9034723 10/1979 Japan ..................................... 560/62

Primary Examiner—Paul J. Killos
Attorney, Agent, or Firm—John H. Shurtleff

[57] ABSTRACT

2-Aryloxy-2-halopropionic acid compounds are prepared by reacting 2-aryloxypropionic acid compounds with N-halocarboxylic acid imides in the presence of aliphatic halohydrocarbons as solvents, and of from 0.0001 to 0.001 mole of halogen per mole of N-halocarboxylic acid imide, from 0.005 to 0.05 per cent by weight of water, based on N-halocarboxylic acid imide, and from 0.0005 to 0.005 mole of azo-bis-isobutyronitrile and/or dibenzoyl peroxide, per mole of N-halocarboxylic acid imide.

The end products obtainable by the process of the invention are valuable starting materials for the preparation of drugs, crop protection agents and dyes.

8 Claims, No Drawings

PREPARATION OF 2-ARYLOXY-2-HALOPROPTONIC ACID COMPOUNDS

The present invention relates to a process for the preparation of 2-aryloxy-2-halopropionic acid compounds by reacting 2-aryloxypropionic acid compounds with N-halocarboxylic acid imides in the presence of aliphatic halohydrocarbons as solvents, and of from 0.0001 to 0.001 mole of halogen per mole of starting material III, from 0.005 to 0.05 percent by weight of water, based on N-halocarboxylic acid imide, and from 0.0005 to 0.005 mole of azo-bis-isobutyronitrile and/or dibenzoyl peroxide, per mole of N-halocarboxylic acid imide.

German Laid-Open Application DOS 2,720,654 discloses that alkanecarboxylic acid derivatives, for example tert.-butyl 4-chlorophenoxyacetate, can be reacted with N-bromosuccinimide in the presence of a solvent and of a source of free radicals, such as dibenzoyl peroxide or azo-bis-isobutyronitrile, to give tert.-butyl bromo-(4-chlorophenoxy)-acetate. In the case of tert.-butyl 4-chlorophenoxyacetate it is stated that a reaction time of 2 hours is required and a yield of 76 percent is obtained. If the process is carried out with the corresponding propionic acid esters, especially on an industrial scale, substantially longer reaction times, for example from 8 to 15 hours, are required to obtain yields of from 60 to 80% of theory.

However, even in the case of acetic acid derivatives, unsatisfactory reaction times and yields must be expected. Acta Chimica Academiae Scientiarum Hungaricae, 79 (1973), 419–432 reports that ethyl 4-chlorophenoxyacetate and N-bromosuccinimide in boiling carbon tetrachloride give a yield of only 52.8 percent of the bromine derivative in spite of using dibenzoyl peroxide as a catalyst, employing a reaction time of 17 hours, and highly activating the reaction by exposure to light.

We have found that 2-aryloxy-2-halopropionic acid compounds of the formula

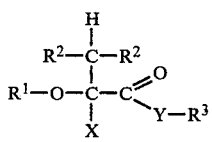

where Y is oxygen or

$R^1$ is an aromatic radical, the $R^2$'s and $R^3$'s can be identical or different and each is hydrogen or an aliphatic or cycloaliphatic radical, and $R^3$ can also be an araliphatic or aromatic radical, and X is chlorine or bromine, are obtained in an advantageous manner by reaction of 2-aryloxypropionic acid compounds with N-halocarboxylic acid imides in the presence of organic solvents, if a 2-aryloxypropionic acid compound of the formula

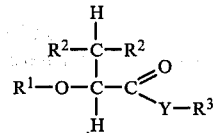

where $R^1$, $R^2$, $R^3$ and Y have the above meanings, is reacted with an N-halocarboxylic acid imide of the formula

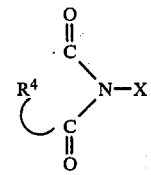

where X has the above meanings and $R^4$ is an aliphatic radical, in the presence of an aliphatic halohydrocarbon as the solvent, and of from 0.0001 to 0.001 mole of halogen, per mole of starting material III, from 0.005 to 0.05 percent by weight of water, based on starting material III, and from 0.0005 to 0.005 mole of azo-bis-isobutyronitrile and/or dibenzoyl peroxide, per mole of starting material III.

If methyl 2-(2',4'-dichlorophenoxy)-propionate and N-bromosuccinimide are used as starting materials, the course of the reaction, in the process according to the invention, can be represented by the following equation:

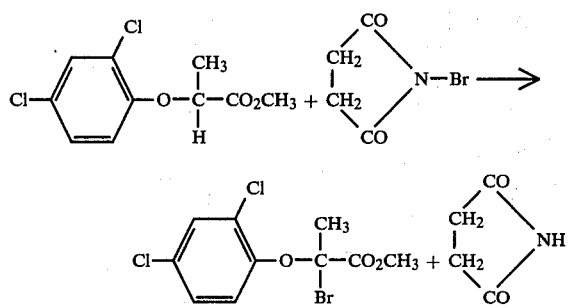

Compared to the conventional processes, the process according to the invention gives 2-aryloxy-2-halopropionic acid compounds more simply and more economically, and with better yield, space-time yield and purity. The reaction time with these propionic acid derivatives is substantially shorter than when the same compounds are prepared by conventional methods. All these advantageous results are surprising, since—especially in the light of the Hungarian publication mentioned—a rather lengthy reaction—particularly since the number of carbon atoms in the alkanecarboxylic acids prepared according to the invention is greater—and a correspondingly low yield would have been expected. In view of the presence of water and the reactivity of the components, side-reactions—of which there is no mention in the above publications, which concern reactions in the absence of water—would also have been expected. Accordingly, the process according to the invention would have been expected to give heterogeneous reaction mixtures, which are difficult to separate, with correspondingly reduced yields and reduced purity of the end product.

Preferred starting materials II and accordingly preferred end products I are those where Y is oxygen or

$R^1$ is phenyl, naphthyl, phenyl which is monosubstituted, disubstituted or trisubstituted by chlorine, bromine, fluorine, nitro, cyano and/or perhaloalkyl or perhaloalkoxy, each of 1 to 6 carbon atoms, or diphenyl which can be substituted in the same manner, the $R^2$'s and $R^3$'s may be identical or different and each is hydrogen, alkyl of 1 to 18, especially of 1 to 8, carbon atoms, or cycloalkyl of 5 to 8 carbon atoms, $R^3$ can also be aralkyl or alkylaryl of 7 to 12 carbon atoms or phenyl which is unsubstituted or is monosubstituted, disubstituted or trisubstituted by chlorine, bromine, fluorine, nitro, cyano and/or perhaloalkyl or perhaloalkoxy, each of 1 to 6 carbon atoms, and X is chlorine or especially bromine. The above radicals can in addition be substituted by atoms or groups which are inert under the reaction conditions, for example alkyl or alkoxy, each of 1 to 4 carbon atoms, or, in the case of aryl radicals, iodine, fluorine, chlorine and/or bromine.

Accordingly, examples of suitable starting materials III are: 2-phenoxypropionic acid which is unsubstituted, or monosubstituted in the 3-position, or disubstituted by identical or different substituents in the 3-position, the substituents being methyl, ethyl, n-propyl, iso-butyl, sec.-butyl, tert.-butyl, n-pentyl, pent-2'-yl, pent-3'-yl, 4'-methyl-pent-3'-yl, 1'-chloroethyl, trifluoromethyl, trichloromethyl, difluoromethyl, nitromethyl, cyanomethyl, 2'-chloroethyl, 1'-chloropropyl, 2'-chloropropyl, 1'-chloro-2-propyl, 1'-fluoroethyl, 2'-fluoroethyl, 1'-fluoro-2'1-propyl, 3'-bromobutyl, 1',1',1'-trifluoroisopropyl, methoxyethyl, methoxyisopropyl, ethoxy-tert.-butyl, methoxy-tert.-butyl, cyclopentyl, cyclohexyl, 2'-chlorocyclohexyl, 2'-chlorocyclohexyl or 2'-(trifluoromethyl)-cyclohexyl; methyl, ethyl, propyl, isopropyl, butyl, isobutyl, sec.-butyl, tert.-butyl, cyclohexyl, cyclopentyl, phenyl and benzyl esters which correspond to the above acids and are unsubstituted or substituted as mentioned above; homologous propionamides which can be substituted in the same way as has been mentioned for the acids, and that in addition the nitrogen of the amide group can be monosubstituted or disubstituted by one or by two identical or different substituents which can be methyl, ethyl, propyl, iso-propyl, butyl, iso-butyl, sec.-butyl, tert.-butyl, cyclohexyl, phenyl or benzyl; and homologous 2-phenoxy compounds which are unsubstituted or substituted as stated above, and are additionally substituted in the 2''-, 3''-, 4''-, 5''- and/or 6''-position of the phenyl nucleus, by one substituent, or by 2 or 3 identical or different substituents, chosen from amongst fluorine, chlorine, bromine, trifluoromethyl, methyl, ethyl, propyl, iso-propyl, butyl, iso-butyl, sec.-butyl, tert.-butyl, methoxy, ethoxy, propoxy, iso-propoxy, butoxy, iso-butoxy, sec.-butoxy, tert.-butoxy, nitro and phenyl.

Particularly preferred starting materials II are methyl 2-(2',4'-dichlorophenoxy)-propionate, ethyl 2-(4'-chlorophenoxy)-propionate, methyl 2-(3'-trifluoromethylphenoxy)-propionate, methyl 2-(4'-chlorophenoxy)-propionate, ethyl 2-(4'-chlorophenoxy)-butyrate, methyl 2-(4'-fluorophenoxy)-propionate, methyl 2-(2'-bromo-4'-chlorophenoxy)-propionate, isooctyl 2-(2', 4'-dichlorophenoxy)-propionate, tert.-butyl 2-(2',4', 5'-trichlorophenoxy)-propionate, methyl 2-(4'-phenylphenoxy)-propionate, ethyl 2-(4'-nitrophenoxy)-propionate, ethyl 2-(2',4'-dichlorophenoxy)-iso-valerate, p-chlorophenyl 2-(3'-trifluoromethylphenoxy)-propionate and 2-(2', 4'-dichlorophenoxy)-propionic acid N,N-dimethylamide.

The reaction is carried out at from $-10°$ to $+150°$ C., preferably from 20° to 120° C., especially from 40° to 120° C., under atmospheric or superatmospheric pressure, continuously or batchwise. The solvents, inert under the reaction conditions, which are used are aliphatic halohydrocarbons, especially chlorohydrocarbons, for example 1,1,2,2- or 1,1,1,2-tetrachloroethane, amyl chloride, dichloropropane, methylene chloride, dichlorobutane, isopropyl bromide, chloroform, 1,1,1- or 1,1,2-trichloroethane, trichloroethylene, pentachloroethane, 1,2-dichloroethane, 1,1-dichloroethane, n-propyl chloride, 1,2-cis-dichloroethylene, n-butyl chloride and 2-, 3- and iso-butyl chloride, preferably carbon tetrachloride and tetrachloroethylene and if desired aliphatic or cycloaliphatic hydrocarbons, for example heptane, cyclohexane, methylcyclohexane, decalin, petroleum ether, hexane or naphtha, or mixtures of the above. The amount of solvent is advantageously from 100 to 10,000 percent by weight, preferably from 500 to 2,000 percent by weight, based on starting material II.

The reaction is carried out in the presence of halogen, as a rule chlorine and especially bromine, in an amount of from 0.0001 to 0.001, preferably from 0.0002 to 0.0006 mole of halogen per mole of starting material III. Preferred N-halocarboxylic acid imides of the formula III and accordingly preferred end products I are those where X is chlorine or especially bromine and $R^4$ is alkylene of 1 to 6, preferably of 2 to 6, especially of 2 to 4, carbon atoms. The above radicals can additionally be substituted by atoms or groups which are inert under the reaction conditions, for example alkyl or alkoxy, each of 1 to 4 carbon atoms. Examples of suitable starting materials III are the N-chloroimides and preferably N-bromoimides of succinic acid, glutaric acid, adipic acid, pimelic acid, suberic acid, azelaic acid and sebacic acid; amongst these, N-bromosuccinimide and N-chlorosuccinimide are preferred. The starting material III can be employed in the stoichiometric amount, less than the stoichiometric amount or in excess, advantageously in an amount of from 0.9 to 2, preferably from 1 to 1.5, moles per mole of starting material II.

Water is used in an amount of from 0.005 to 0.05, especially from 0.005 to 0.01, percent by weight based on starting material III. Water can be added separately to the starting components; advantageously, it is added as a mixture with the halogen and a proportion of the halohydrocarbon used. Advantageously, a solution containing from 0.1 to 3, especially from 0.5 to 1, percent by weight of chlorine or of bromine in the particular halohydrocarbon is employed, water being added to this solution until it is saturated. The free radical donor azo-bis-isobutyronitrile or dibenzoyl peroxide is advantageously used in an amount of from 0.001 to 0.005 mole per mole of starting material III.

The reaction can be carried out as follows: A mixture of starting material II and III, together with halogen, water, solvent and free radical donor is kept for from 0.5 to 5 hours at the reaction temperature. The end product I is isolated from the reaction mixture in a conventional manner, for example by fractional crystallization.

The end products I obtainable by the process according to the invention are valuable starting materials for the preparation of drugs, crop protection agents and dyes. Concerning their use, reference may be made to the publications mentioned earlier.

In the Examples which follow, parts are by weight.

EXAMPLE 1

A saturated aqueous solution of 0.01 part of bromine and one part of carbon tetrachloride is added to a mixture of 37.5 parts of methyl 2-(2',4'-dichlorophenoxy)-propionate, 26.7 parts of N-bromosuccinimide, 0.1 parts of azo-bis-isobutyronitrile and 300 parts of carbon tetrachloride. After 45 minutes of heating, 0.1 part of azo-bis-isobutyronitrile and 0.01 part of bromine in 1 part of carbon tetrachloride are added, at 70° C., and the batch is then stirred for 45 minutes at 77° C. It is then cooled to 40° C. and filtered, and the filtrate is concentrated under reduced pressure. 45 parts (91.5% of theory) of methyl 2-bromo-2-(2',4'-dichlorophenoxy)-propionate, of $n_D^{22} = 1.5390$, are obtained.

EXAMPLE 2 (COMPARATIVE EXAMPLE)

37.5 parts of methyl 2-(2',4'-dichlorophenoxy)-propionate and 26.7 parts of N-bromosuccinimide in 300 parts of carbon tetrachloride are boiled under reflux, 0.1 part of azo-bis-isobutyronitrile being added every 45 minutes. The mixture is refluxed until the succinimide formed floats on the solvent. A total reaction time of 10 hours is required. The mixture is then cooled to 0° C. and filtered, and the filtrate is concentrated under reduced pressure. 36.9 parts (82% of theory) of methyl 2-bromo-2-(2',4'-dichlorophenoxy)-propionate, of $n_D^{22} = 1.5395$, are obtained.

We claim:

1. A process for the preparation of 2-aryloxy-2-halopropionic acid compounds of the formula

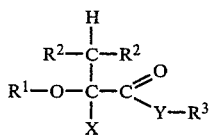

I where Y is oxygen or

$R^1$ is an aromatic radical, the $R^2$'s and $R^3$'s can be identical or different and each is hydrogen or an aliphatic or cycloaliphatic radical, and $R^3$ can also be araliphatic or aromatic radical, and X is chlorine or bromine, by reacting a 2-aryloxypropionic acid compound with an N-halocarboxylic acid imide in the presence of an organic solvent, wherein a 2-aryloxypropionic acid compound of the formula

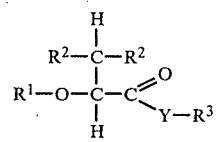

II where $R^1$, $R^2$, $R^3$ and Y have the above meanings, is reacted with an N-halocarboxylic acid imide of the formula

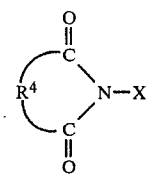

III where X has the above meanings and $R^4$ is an aliphatic radical, in the presence of an aliphatic halohydrocarbon as the solvent and of from 0.0001 to 0.001 mole of halogen per mole of starting material III, from 0.005 to 0.05 percent by weight of water, based on starting material III, and from 0.0005 to 0.005 mole of azo-bis-isobutyronitrile and/or dibenzoyl peroxide per mole of starting material III.

2. A process as claimed in claim 1, wherein the reaction is carried out at from −10° to +150° C.

3. A process as claimed in claim 1, wherein the reaction is carried out at from 20° to 120° C.

4. A process as claimed in claim 1, wherein the reaction is carried out in the presence of from 100 to 10,000 percent by weight of solvent, based on starting material II.

5. A process as claimed in claim 1, wherein the reaction is carried out in the presence of from 0.0002 to 0.0006 mole of halogen per mole of starting material III.

6. A process as claimed in claim 1, wherein the reaction is carried out with from 0.9 to 2 moles of starting material III per mole of starting material II.

7. A process as claimed in claim 1, wherein the reaction is carried out in the presence of from 0.005 to 0.01 percent by weight of water, based on starting material III.

8. A process as claimed in claim 1, wherein the reaction is carried out with from 0.001 to 0.005 mole of a free radical donor per mole of starting material III.

* * * * *

UNITED STATES PATENT AND TRADEMARK OFFICE
CERTIFICATE OF CORRECTION

PATENT NO. : 4,348,534
DATED : September 7, 1982
INVENTOR(S) : Gerd Husslein and Gerhard Hamprecht It is certified that error appears in the above-identified patent and that said Letters Patent are hereby corrected as shown below:

On the title page and the first page, in both cases,
change the title of the invention from
"Preparation of 2-Aryloxy-2-Haloproptonic Acid Compounds"
to --Preparation of 2-Aryloxy-2-Halopropionic Acid
Compounds--.

Signed and Sealed this

Fifteenth Day of February 1983

[SEAL]

Attest:

GERALD J. MOSSINGHOFF

Attesting Officer   Commissioner of Patents and Trademarks